United States Patent [19]

Elmes et al.

[11] Patent Number: 5,021,462
[45] Date of Patent: Jun. 4, 1991

[54] POROUS MATERIAL AND ITS PREPARATION

[75] Inventors: Alfred R. Elmes; Kevin Hammond, both of Wirral, England; David C. Sherrington, Kirkintilloch, Scotland

[73] Assignee: Unilever Patent Holdings B.V., Rotterdam, Netherlands

[21] Appl. No.: 606,937

[22] Filed: Oct. 31, 1990

Related U.S. Application Data

[62] Division of Ser. No. 185,671, Apr. 25, 1988, Pat. No. 4,985,468.

[30] Foreign Application Priority Data

Apr. 24, 1987 [GB] United Kingdom ............... 8709688

[51] Int. Cl.$^5$ .................................................. C08J 9/28
[52] U.S. Cl. .................................... 521/63; 521/64; 521/61
[58] Field of Search .................................... 521/63, 64

[56] References Cited

U.S. PATENT DOCUMENTS

| Re. 27,444 | 7/1972 | Will | 521/62 |
| 3,763,056 | 10/1973 | Will | 521/62 |
| 3,822,224 | 7/1974 | Gillan | 521/63 |
| 3,879,314 | 4/1975 | Gunning et al. | 521/62 |
| 3,891,577 | 6/1975 | Kershaw et al. | 521/62 |
| 3,923,704 | 12/1975 | Gunning et al. | 521/62 |
| 3,933,579 | 1/1976 | Kershaw et al. | 521/62 |
| 4,399,237 | 8/1983 | Morrison, Jr. | 521/64 |
| 4,461,848 | 7/1984 | Lawson et al. | 521/64 |
| 4,797,425 | 1/1989 | Kishing et al. | 521/64 |

FOREIGN PATENT DOCUMENTS

| 1162215 | 8/1969 | United Kingdom . |
| 2143536 | 2/1985 | United Kingdom . |

OTHER PUBLICATIONS

European Search Report for 88303675.8–Unilever PLC et al.
2464 Cellular Polymers, vol. 2 (1983) No. 4, Great Yarmouth, GB pp. 295–298–Letters to the Editor, "Micro-/Macrocellular Concept for Foamed Polymers", A Gill, Diamond Shamrock.

*Primary Examiner*—Morton Foelak
*Attorney, Agent, or Firm*—Cushman, Darby & Cushman

[57] ABSTRACT

A porous polymeric material has cell sizes within the range 100 to 0.5 μm and total pore volume with respect to the overall volume of the material in the range 75 to 98% and includes cross-linked polycondensation polymeric material. The material can be made from a high internal phase emulsion in which the cross-linked polycondensation polymer is formed in the continuous phase. The materials are preferably open interconnected cellular structures. They can be made of a wide range of polycondensation materials. The materials are thus highly porous and light weight and have a range of properties depending primarily on their constituent polycondensation materials.

7 Claims, No Drawings

POROUS MATERIAL AND ITS PREPARATION

This is a continuation division of application No. 07/185,671, filed Apr. 25, 1988 now U.S. Pat. No. 4,985,468.

The present invention relates to a porous material and to a process for its preparation. In particular the present invention relates to a porous material whose total pore volume with respect to the overall volume of the material is within the range 75 to 98% and to a process involving the preparation of a high internal phase emulsion.

It has previously been proposed in U.S. Pat. No. 4,039,489 to prepare relatively low density oil absorbent polymeric materials in the form of polystyrene and polyurethane foams using various foaming agents. In British Patent No. 1,291,649 proposals have been made to prepare a relatively low density, oil absorbent, polymeric foam by the inclusion of a volatile material into a pre-polymer and then rapidly reducing pressure and permitting the volatile material to expand the polymeric material to generate the foam.

In U.S. Pat. No. 3,988,508 Lissant has disclosed the production of polymeric materials by polymerisation of an oil-in-water emulsion system having a high internal phase ratio of monomer to water, preferably 85-95%, although the disclosure is of monomer water ratios in the range 20:80 to 95:5 without a cross-linking agent.

The study of high internal phase emulsions has been carried out for many years and the basic theory behind their preparation and structure has been discussed by K. J. Lissant in "Surfactant Science Series", Volume 6, "Emulsion and Emulsion Technology", Part 1, edited by K. J. Lissant, Marcel Dekker Inc., N.Y., 1974. In this work Lissant discusses the geometrical packing of droplets in high internal phase emulsions and suggests that especial care must be exercised in selecting emulsifying agents for such compositions and that, in the region of 94-97% volume percentage of internal phase, critical changes occur in the high internal phase emulsion (HIPE). Beerbower, Nixon, Philippoff and Wallace of Esso Research and Engineering Company have studied high internal phase emulsions as safety fuels, such compositions containing at least 97% by weight of hydrocarbon fuel (ref. American Chemicals Society, Petrochemical Pre-prints, 14, 79-59, 1969).

In U.S. Pat. No. 3,255,127, polymeric materials are disclosed which are prepared by polymerisation in reversed emulsion. In this specification a relatively small proportion of water is emulsified into a mixture of emulsifier, catalyst and monomer and the emulsion so produced is mixed into a far larger proportion of water, usually containing a stabiliser such as polyvinyl alcohol, which keeps the droplets of reversed emulsion in a relatively stable form. Polymerisation takes place in a period of the order of 24 hours at 55° C. to yield particulate polymer or polymer block which can readily be broken down to give a particulate polymer.

In British Patent No. 1,576,228 AKZO disclosed the production of thermoplastic microporous cellular structures comprising microcells having an average diameter of 0.5-100 microns with smaller diameter pores connecting the microcells. These structures are made by dissolving a suitable thermoplastic polymer in a solvent at elevated temperature and then cooling the solution to solidify the polymer and then removing the liquid from the thermoplastic polymer structure. This process is clearly limited in its application to polymers which can readily be dissolved in appropriate solvents.

In British Patent No. 1,513,939, Ceskoslovenska Akademie Ved also disclosed the production of porous polymers, but these are formed as porous beads which may be coalesced to form a moulding which will clearly not be homogeneous or uniform in its porosity. The porous beads are prepared by dissolving the polymer to be used in a solvent and then dispersing the solution into a compatible carrier liquid and this mixture is added to a coagulating liquid such as water to precipitate the porous beads of polymer. This process is also limited in that if cross-linked polymers are desired they can only be produced by a random linking of pre-formed linear polymer chains.

British Specification No. 2,000,150 discloses the production and use of cross-linked polymeric porous beads. The beads may be used to extract components from liquid mixtures and typically have a pore volume of 2.42 ml/g and are hard enough to be packed into absorbency columns.

British Specification No. 1,458,203 suggests the preparation of shaped cellular articles by curing an emulsion containing up to 90 parts by weight of water to 10 parts by weight of polymerisable mixture.

In British Patent No. 1,428,125, ICI commented on the desirability of maximising the water content of water extended polymers, but they suggest that difficulty was experienced in obtaining water-in-oil emulsions with water contents in excess of 88% by weight water.

Our earlier EP patent specification No. 0060138 suggests the preparation of a porous homogeneous material from a high internal phase emulsion using a cross-linked vinyl polymer material.

It is an object of the present invention to provide a novel highly porous polymeric material. It is a further object of the present invention to provide a novel highly porous polymeric material that can be made by a process that can be readily adapted to continuous or semi-continuous production methods.

According to a first aspect of the present invention there is provided a porous cross-linked polymeric material having cell sizes within the range 100 to 0.5 μm and total pore volume with respect to that of the overall volume of the material in the range 75 to 98% wherein the polymeric material includes cross-linked polycondensation polymeric material.

Thus the present invention provides a highly porous cross-linked polycondensation material having cell sizes within the range 100 to 0.5 μm. The present materials thus differ from conventional foamed for example polyurethane materials whose cell volumes range from a minimum of about 200 μm to a selected higher value for example 500 μm. The present cross-linked materials also differ significantly from those disclosed in GB No. 1576228 which by necessity are thermoplastic and non-crosslinked.

The present materials preferably have a total pore volume with respect to that of the overall volume of the material of at least 85%, more preferably of at least 90%.

The present materials preferably comprise a structure of interconnecting cells. The material can thus be very light and can for example have an overall density of less than 0.25 g/cm³. A realistic minimum overall density for a material of 98% overall porosity will be of the order of 0.02 g/cm³.

In principle there is no inherent restriction on the polycondensation polymer comprising the present materials. The polycondensation polymer can thus be chosen from a wide range of materials. For example the polycondensation polymer can give either a hydrophilic or a hydrophobic characteristic to the porous polymeric material, and if desired, functional groups can be present in the polycondensation polymeric material.

The present polymeric materials can thus have a high porosity and permeability in combination with a resistance to chemical attack and dissolution due to their cross-linked nature, the degree of cross-linking being at least such that the materials retain an integral three-dimensional matrix even in a solvent swollen state. A range of mechanical characteristics e.g. tensile strengths, and thermal stability can moreover be imparted to the material, depending primarily on the particular polycondensation material selected. Such a combination of properties at a cell size of 0.5 to 100 μm provides a novel material for which many advantageous uses can be envisaged.

Examples of such uses include use as a filter body in a wide variety of environments, use as a carrier for example for a range of catalysts in a wide variety of physical and chemical environments, and use as a containment system for example a range of toxic materials in liquid form. For use as a containment system the present porous materials can either be prepared having open interconnected cells allowing the toxic or other liquid to be absorbed to provide a non-spill container or, alternatively, the porous materials can be prepared having a closed cell system with the toxic or other liquid comprising the dispersed internal phase and thus being immediately contained within the porous polymeric material as it is formed providing a non-spill and non-evaporating containment system.

The present materials can moreover be substantially homogeneous and can be present in a monolithic block form, particulate form or for instance an extruded sheet or strand form. The integral nature of the material again allows a wide variety of uses for the material to be contemplated.

The polycondensation polymeric material can be derived from a monomer and/or pre-polymer or mixtures thereof having at least two different reactive groups. In other words the polycondensation species formed can be of the type —(X—Y)$_n$— in which X and Y are derived from the reactive groups. Alternatively the polycondensation polymeric material can be derived from at least two types of monomers or pre-polymers. In other words the polycondensation species formed is of the type —(—X—X—Y—Y—)$_n$— in which X and Y are derived from the respective reactive groups on two types of monomer or pre-polymer X'—X' and Y'—Y'. In some cases the polymeric material can be formed by ring-opening reactions of cyclic molecules e.g. of the type

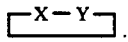

By pre-polymer we mean a pre-polymerised group of monomers which can be chain extended by a polycondensation reaction to form the polycondensation polymeric material. Cross-linking is inherent due to the number of reactive groups on the monomer or prepolymer or can be introduced by appropriate cross-linking agents. The monomers and/or pre-polymers can be branched and/or straight chain.

Chain-extension or cross-linking can occur by the addition of other reactive components. For example, poly-condensation cross-linking can occur by the addition of formaldehyde to a pre-polymer or polymer such as formed from phenol formaldehyde. Generally the pre-polymers employed will have a molecular weight within the range 200 to 100,000 and/or chain length of 2 to 1,000 units, preferably 200 to 20,000 molecular weight and/or chain length of 2 to 200 units.

A great variety of polymers can be produced by the present process. Suitable polycondensation reactions are exemplified by the descriptions in "Condensation Polymers" P. W. Morgan Interscience New York 1965. The present polymers are suitably derived from synthetic materials, particularly those obtained from fossil sources e.g. coal or petrochemical sources or inorganic sources. The present polymers can however be derived from materials derived from natural sources, which can if desired by modified e.g. cellulose acetate. Mixtures of sources can be employed.

Particular examples of polycondensation polymeric materials which can be employed in the present invention include the polycondensation products between urea and aldehydes, the polycondensation products between phenols and aldehydes, the polycondensation products between resorcinols and aldehydes, polyvinyl formals, polyesters, polyamides, polyacetals, polyurethanes, polysiloxanes, polyimides, polybenzimidazoles, polyethers, polythioethers, polyketals, polyether sulphones and polyether ketones and mixtures thereof.

The present polymeric materials can have an overall density of less than 0.25 g/cm$^3$. A minimum overall density will be of the order of 0.02 g/cm$^3$. These figures as well as those relating to cell size and pore volume relate to the initially formed polymeric material. On washing and drying, the material may collapse resulting in a change in pore dimensions. On placing in a solvent the material may swell, again resulting in a change of pore dimensions.

Preferably, the cell sizes can be within the range of 50 to 5 μm, more preferably 20 to 0.5 μm, even more preferably 10 to 0.5 μm. The cell sizes can be uniform and readily be of the order of 3.5 μm. Although some few cells may be present with a size below 0.5 μm, the vast majority will have diameters within the range 100 to 0.5 μm. Preferably the cells are interconnected by a plurality of holes in the walls of the pores. The holes can be of the order of 8 to 16 per cell or the number of holes per cell can be very much greater. The holes can be of a size in the range of 0.2 to 0.05 cell diameter.

The present invention can thus provide a highly porous, absorbent, and light-weight material. The materials can be generally homogeneous. Materials can be formed having a dry density of less than 0.25 g/cm$^3$, even less than 0.1 g/cm$^3$, a pore volume of more than 3 cm$^3$/g and an adsorbency for liquids defined in terms of oleic acid of at least 2.5 cm$^3$/g.

According to a second aspect of the present invention there is provided a process for preparing a porous polymeric material comprising preparing an emulsion whose internal phase comprises 75 to 98 volume % of the material and consists of globules having dimensions in the range 100 to 0.5 μm and forming in the continuous phase a cross-linked polycondensation polymer.

Preferably the internal phase is removed e.g. by washing and drying, the latter if necessary vacuum assisted.

The formation of the polycondensation polymer can occur spontaneously or can suitably be initiated by the addition of an acid or base, as appropriate, and/or by heating the emulsion. Polycondensation reactions can be relatively fast. Cooling can be employed to control the reaction rate.

In one embodiment it is therefore necessary to form the emulsion first having its internal phase of the desired dimensions and then for example to stir acid or base into the emulsion and, if necessary, heat.

In another embodiment when the reaction is sufficiently slow the emulsion can be formed containing all the necessary components and the reaction allowed to proceed, if necessary by heating.

In another embodiment the already formed emulsion containing a reactant in the continuous phase, and if necessary an acid or base as catalyst, can be brought into contact with the other reactant which then diffuses into the continuous phase and interacts with the first reactant to form the cross-linked polycondensation polymeric material. Suitably the other reactant is dissolved in an inert solvent and the prepared emulsion is added to or extruded in sheet like form into the solution. Alternatively the other reactant could be in gaseous form.

Where two or more reactants are present in the ready formed emulsion they can each be in the continuous phase, or possibly they can be split between the two phases. In the latter case one or more reactants can be initially dissolved in one phase and other reactant in the other phase prior to preparing the emulsion.

Cross-linking is present in the final product either inherently due to the number of reactive groups on the monomer or prepolymer or by the presence of appropriate cross-linking agents, for example polycondensation cross-linking agents.

In order to prepare the emulsion generally an emulsifier can be present, suitably in a concentration in the range 0.1 to 25% by weight with respect to the continuous phase. Suitable emulsifiers include amphoteric emulsifiers such as Miranol C2M-SF and Admol Wol, Span 80, Tween 20, sucrose esters, and mono-oleate type emulsifiers. Either in the presence or absence of emulsifiers the emulsion having appropriate size of its internal phase can be achieved by stirring using for example a conventional paddle stirrer.

The reactants are suitably present in the emulsion at a concentration of 2 to 100 wt % with respect to the continuous phase. The emulsion phases can be derived from any two immiscible materials. The only requirement is that the phase or phases carrying the reactant materials are able to dissolve or disperse the reactant materials in question. The continuous phase can for example be water or an organic solvent such as for example a hydrocarbon or a chlorocarbon. Alternatively the continuous phase can consist of one or more of the initial reactants.

The present process can be employed to prepare the present polymeric products. The reaction times can be nearly instantaneous from for example the point of the addition of the catalyst or the contacting of spontaneously reactive components. In practice a minimum reaction time of about 5 minutes has proved practical with a maximum time being about 6 hours. In some instances somewhat longer times may be required. Nonetheless it can be seen that the present process can lend itself to production on a continuous or semi-continuous process. It can moreover be adept at allowing homogeneous products to be produced in a wide variety of shapes or sizes. The products can for example be formed in integral blocks in moulds or in sheet, strand or granule form by extrusion. Particulate material can be formed by granulating for example blocks of the material.

Appropriate starting materials for the present process are those described above. Similarly the preferred process conditions are those to provide the preferred materials mentioned above. For example process conditions preferably include an internal phase of at least 85% by volume, more preferably at least 90% by volume, and having globule dimensions within the range 20 to 0.5 $\mu$m, more preferably 10 to 0.5 $\mu$m.

The present invention can thus provide a highly porous cross-linked polycondensation material having cell sizes within the 100 to 0.5 $\mu$m which is made from a high internal phase emulsion.

Embodiments of the present invention will now be described by way of example only with reference to the following Examples.

EXAMPLE 1

Resorcinol (8.3 g; 0.075 mol) and formalin (40% aq; 12.2 g; 0.15 mol formaldehyde) were added to a polyethylene jar and heated to 30° C. to form a homogeneous solution. After cooling to room temperature an amphoteric emulsifier, MIRANOL C2M-SF. CONC (37% aq; 2.3 g) was added. The resulting clear solution was stirred with a paddle stirrer while cyclohexane (180 ml) was added dropwise over a period of 30 minutes to form a thick high internal phase emulsion. An acidic catalyst, phosphoric acid (50% aq; 3.0 g) was then stirred into the emulsion. An opaque rigid polymer was formed after heating at 60° C. for ten minutes. The water and cyclohexane were removed at 75° C. in a vacuum oven.

The resulting porous polymeric material was tough, hydrophobic and salmon pink in colour. Examination of the material by scanning electron microscopy showed it to have a structure comprising a matrix of interconnecting cells having diameters within the range 1 to 15 $\mu$m. The material had an overall porosity of 90% by volume, a density of about 0.1 g cm$^{-3}$, a compressive strength of about $9 \times 10^5$ Nm$^{-2}$ and a permeability of about 0.1 Darcys.

EXAMPLE 2

The same procedure was used as described in Example 1. 3.0 g of resorcinol and 4.1 g of formalin were employed. The emulsifier was hexadecylpropyl sulphobetaine ($nC_{16}H_{33}N^+(CH_3)_2(CH_2)_3SO_3^-$) (0.14 g) and the emulsion dispersed phase was heptane (100 ml). Addition of the catalyst p-toluenesulphonic acid (70% aq; 1.0 g) produced a rigid polymer after 3 minutes at room temperature, and polymerisation was completed by heating to 60° C. for 30 minutes. Water and heptane were removed at 75° C. under vacuum.

The resulting porous polymeric material had similar physical properties to the product of Example 1.

EXAMPLE 3

The same procedure was used as described in Example 1. 3.0 g of resorcinol and 7.9 g of glyoxal (40% aq) were employed. The emulsifier was MIRANOL C2M-SF. CONC (37% aq; 1.2 g) and the emulsion dispersed phase was petroleum ether (60 ml, 100–120 B.Pt). Addition of the catalyst, p-toluenesulphonic acid (70% aq; 1.0 g) followed by heating to 80° C. for 2 hours produced a rigid polymer. The water and petroleum ether were removed at 100° C. under vacuum.

The material had a porosity of about 90% by volume and cell sizes falling within the range 1 to 15 μm.

EXAMPLE 4

The procedure of Example 1 was followed with the exception that 5-methylresorcinol in place of resorcinol and the basic catalyst, sodium carbonate (20% aq; 2.0 g), in placeof the acidic catalyst, phosphoric acid, were employed. A rigid polymer formed within 20 minutes at room temperature. Polymerisation was completed by heating for 30 minutes at 60° C. Water and cyclohexane were removed in a vacuum oven.

The resulting polymeric material had a porosity and other physical characteristics similar to the product of Example 1.

EXAMPLE 5

A two stage procedure was employed to produce a urea-formaldehyde based porous polymer. A pre-polymer syrup was prepared initially. Formalin (40% aq; 81 g 1.0 mol), sodium acetate (0.4 g) and concentrated ammonia (S.G. 0.88; 0.8 g) were mixed to form a homogeneous solution. Urea (30 g; 0.5 mol) was then added slowly, and the mixture heated and stirred slowly to 90° C. for 30 minutes. This temperature was then maintained for 2 hours during which time the solution became cloudy. 35 ml of water was then distilled out to yield a turbid pre-polymer syrup (70% solids). The pH of the syrup was adjusted to 7.4 with a few drops of 0.5M NaOH to stabilise the product. In the second step this syrup (12.3 g) was mixed with a surfactant, MIRANOL C2M-SF. CONC (37% aq; 1.4 g), and cyclohexane (160 ml) stirred into the mixture to form a high internal phase emulsion. Curing of the pre-polymer was then induced by stirring in ammonium chloride (40% aq; 1.0 g) and heating for 2 hours at 50° C. The rigid polymer thus formed was dried at 75° C. in a vacuum oven.

The resulting urea-formaldehyde polycondensation material had an overall porosity of 93% by volume and, as shown by scanning electron microscope pictures, an interconnected cellular structure in which the cells had an average diameter of approximately 12 μm. The material was prepared in block form, but could if desired be readily granulated.

EXAMPLE 6

An alternative one stage version of Example 5 is as follows. A solution of formalin (40%; 16.2 g; 0.20 mol), urea (6.0 g; 0.10 mol) and MIRANOL C2M-SF. CONC (2.5 g) was prepared and solid ammonium chloride (2.0 g) added. Cyclohexane (197 ml) was stirred in slowly to form a high internal phase emulsion. The emulsion was heated to 50° C. for 30 minutes then left overnight at room temperature to produce a rigid polymer. The polymer was dried as in Example 5.

The resulting material had similar properties to the product of Example 5.

EXAMPLE 7

A phenol-formaldelyde porous polymeric material was prepared in a two-stage process, the first involving the preparation of a pre-polymer.

A mixture of formalin (40% aq; 55 ml; 0.79 mol), phenol (30 g; 0.32 mol) and sodium hydroxide (30% aq; 1.3 ml) was refluxed for one hour, followed by cooling to room temperature. The pH of the resulting mixture was adjusted to pH 7.4 with a few drops of molar lactic acid and the mixture separated into two distinct phases. Water and excess formaldehyde were removed by rotary evaporation to leave a clear pre-polymer syrup.

A high internal phase emulsion was produced by the dropwise addition, with stirring, of heptane (170 ml) to a mixture of pre-polymer (15 g), water (8 ml) and Miranol C2M-SF. CONC surfactant (2.6 g). Curing was brought about by the addition of toluene-4-sulphonic acid (70% aq; 4.0 g) followed by heating for 2 hours at 70° C. Drying of the resulting material was carried out by heating at 100° C. in a vacuum oven.

The resulting phenol formaldehyde polycondensation polymer was recovered as an opaque solid which was hydrophobic in nature. Mechanically the material was very tough. Assessment of the material by scanning electron microscopy showed it to consist of an open interconnecting cellular structure in which the cells had a diameter within the range 0.2 to 7.0 μm. The material had an overall porosity of approximately 90% by volume.

EXAMPLE 8

The procedure of Example 7 was repeated employing 3-aminophenol in place of phenol.

3-aminophenol (6.0 g; 0.055 mol) was dissolved in a solution of sodium hydroxide (2.4 g; 0.060 mol) in water (1.0 g). The resulting phenoxide solution was cooled to below 10° C. and then formalin (40% aq; 8.3 g; 0.11 mol) was added incrementally to form a pre-polymer syrup. In order to prevent premature resinification the temperature was kept below 15° C.

An emulsifier, Miranol C2M-SF Conc (37% aq; 2.8 g) was stirred into the pre-polymer syrup followed by petroleum ether (180 ml; 100°–120° C. B.P.) to form a high internal phase emulsion. The emulsion was heated to 80° C. for an hour. The resulting polymer was porous and rigid and had cell sizes within the range of approximately 2 to 25 μm and holes interconnecting the cells having diameters within the range of approximately 0.05 to 6 μm.

EXAMPLE 9

A polyvinyl formal porous polymer was prepared by cross-linking a polyvinyl alcohol. Polyvinyl alcohol (9.0 g), formalin (40% aq; 14 g), water (22.3 g) and Miranol C2M-SF. CONC (2.2 g) were mixed at 90° C. to form a viscous solution. Liquid paraffin (240 mls) was added with stirring to form a high internal phase emulsion. An acid catalyst hydrochloric acid (10M; 6.2 g) was slowly added with stirring and the resulting mixture was incubated at 60° C. for 8 hours. The resulting porous polymer was washed free of liquid paraffin.

The resulting porous polymer was hydrophilic and in a hydrated state was soft in texture with elastic properties. On drying the porous polymer showed slight homogeneous shrinkage and an increase in rigidity.

The hydrated polymer material had cell diameters within the range 5 to 20 μm and an overall porosity of approximately 90% by volume.

EXAMPLE 10

A mixed polycondensation polymeric material was prepared.

The first stage of Example 7 was followed to yield a clear pre-polymer phenol formaldehyde syrup. 20 parts by weight of this syrup were admixed with 80 parts by weight of a polyvinyl alcohol-formalin containing viscous solution described in Example 9. A high internal phase emulsion was prepared from this admixture by adding with stirring liquid paraffin. Acid catalyst, toluene-4-sulphonic acid (70% aq), was added to the emulsion which was then allowed to cure at 80° C. for 8 hours.

After extracting the liquid paraffin the resulting porous polymeric material was tough and rigid in the dry state. The hydrated polymer had cells of a similar size to the product of Example 9, but was somewhat firmer and less elastic.

EXAMPLE 11

A melamine-formaldehyde based porous polymer was prepared by a two step method similar to Example 5. Melamine (63 g; 0.5 mol) was added to neutralised (pH 7-7.5) formalin (40% aq; 113 g; 1.5 mol). Ammonia solution (0.880; 1.3 ml) was added and the mixture stirred and heated to boiling. The resulting homogeneous solution was refluxed for 40 minutes, then concentrated under reduced pressure to give a clear, viscous syrup (70% solids). An aliquot of this syrup (12.2 g) was diluted with glycerol (2.3 g) and Miranol C2M-SF. CONC (1.5 g). Heptane 100 ml) was stirred in slowly to form a high internal phase emulsion. Phosphoric acid (50% aq; 1.0 g) was mixed in and the catalysed emulsion heated at 70° C. for an hour.

The resulting polymeric material was further heated at 150° C. under vacuum to dry it and complete the cure.

The final polycondensation material was rigid and comprised an open cellular structure. The cells had a diameter within the range 1 to 12 μm. The material had an overall porosity of approximately 88% by volume.

EXAMPLE 12

A polycondensation polymeric porous material embodying the present invention was prepared using as a starting material a commercially available epoxy adhesive resin. A xylene solution of the epoxy resin and hardener containing the water-in-oil emulsifier Span 80 was prepared. Water was stirred into the xylene solution in a ratio of water to xylene solution of 90:10 to form a high internal phase emulsion with water as the dispersed phase. The emulsion set to a hard rigid prous polymer in about 12 hours at room temperature. The porous polymer had an overall porosity of about 90% by volume and interconnecting cells having diameters within the approximate range of 1 to 30 μm.

EXAMPLE 13

A polyamide based porous cross-linked polymer was prepared by injecting a high internal phase emulsion containing a diamine into an organic phase containing a triacid chloride. Hexamethylene diamine (2.3 g), triethylamine (4.4 g) and Miranol C2M-SF. CONC (37% aq; 1.2 g) were mixed together. Cyclohexane (80 ml) was stirred into this mixture to form an emulsion. A receiving phase consisting of 1,3,5-benzenetricarboxylic acid chloride (3.5 g) in toluene (20 ml) was prepared. The emulsion was introduced into a glass syringe, and thence extruded into the receiving phase. Polymer was formed when the reagents were contacted and they were allowed to react for a further hour at room temperature. The resulting porous polymer was washed with water and ether, and dried under vacuum.

The polyamide (nylon 6,6) material recovered was in the form of threads and granules as a result of the extrusion approach to its preparation. Mechanically the polycondensation material was found to be tough, but also rather brittle. Scanning electron microscopy analysis showed the material to have an interconnected open cell structure, with the cells having a diameter within the range 1 to 10 μm. The dried material had an overall porosity of approximately 90% by volume.

EXAMPLE 14

The procedure of Example 13 was repeated using in place of the hexamethylene diamine, m-phenylene diamine (2.2 g).

The resulting porous polymer had similar physical properties to those of Example 13.

EXAMPLE 15

A silicone based porous polymer was prepared by cross-linking a linear siloxane pre-polymer. Silicone pre-polymer B (J-SIL Silicones (UK), 11.5 g) which is a room temperature vulcanizable silicone elastomer comprising silanol capped polysiloxane, SILESTER OS (Monsanto, 8.0 g) which is a polymeric alkyl silicate containing the equivalent of 40% $SiO_2$, and two surfactants, ARLACEL 987 (a sorbitan mono-oleate having an HLB of 4.3; 1.8 g) and SPAN 85 (a sorbitan monoisostearate having an HLB of 4.3; 1.8 g), were mixed together. The catalyst dibutyl tin dilaurate (0.5 g) was added as the last component of this phase. Water (130 ml) was stirred in by hand to form a high internal phase emulsion over a period of 15 minutes. The emulsion was then left to cure for a further 30 minutes at room temperature before it became rigid, while remaining flexible. After further curing at room temperature overnight, and drying at 60° C. in a vacuum oven, a soft porous silicone based polymer was obtained.

The resulting polysiloxane, silicone based, polymer had an open cellular structure with the constituent cells having an average diameter of about 10 μm. The material was opaque, soft and flexible in nature and exhibited a snappy elastic return. The material had an overall porosity of approximately 80% by volume.

EXAMPLE 16

A proteinaceous porous polymer was prepared by cross-linking a macromolecular structured polyamide bovine serum albumin.

Bovine serum albumin was dissolved in an aqueous phase at a concentration of 30 wt %. An oil-in-water emulsion having an internal phase of 86% by volume was formed by the addition with stirring of light liquid paraffin in the presence of Miranol C2M-SF. CONC (2 g per 100 ml reaction mixture). Aliquots of the high internal phase emulsion were dialysed against 50 wt % gluteraldehyde solution.

The resulting cross-linked polymeric material had an open cellular structure which allowed the internal oil phase to be removed and the material to be washed and dried. On drying a small amount of homogeneous shrinkage occured. The dried material was self-supporting, hard and brittle.

Prior to drying the porous material had an overall porosity of approximately 86% by volume and comprises interconnected cells having diameters within the range 1 to 20 μm.

Tests were performed on each of the above products to show the cross-linked nature of the polycondensation porous materials. Each product was subjected to a series of tests in order to assess its solubility with respect to a range of solvents. Each test was performed by covering approximately 50 mg of the product with 3 to 5 ml of the test solvent in a test tube and leaving overnight. The effect of the solvent on the products after the respective time was noted. Each product was subjected to a dissolution test in each of: water, toluene, chloroform, dimethylformamide; concentrated (98%) sulphuric acid ($H_2SO_4$), acetone, and in some cases m-cresol. The toluene and m-cresol tests involved heating in a bath held at 80° C. for 6 hours.

By way of comparison equivalent tests were performed on a range of porous polycondensation materials that were known to be not cross-linked. These materials were prepared by the method disclosed in GB1576228 (AKZO) in which it is an essential feature of the preparative method disclosed that the resulting polymeric materials are thermoplastic and soluble. Two of the comparative materials tested were examples of materials obtained commercially from AKZO and thus made by AKZO.

The comparative materials employed and produced according to the method disclosed in GB1576228 were: A. polyethylene; B. polypropylene (commercially available sample); C. polystyrene; D. synthetic butyl rubber (70% butadiene content); E. ethylene/acrylic acid salt copolymer (>40% $CO_2Na$); F. polycarbonate (from Bisphenol A); G. polyphenylene oxide; H. nylon 6 (commercially available sample); I. nylon 66; J. nylon 11.

The results of the tests are given in the Table below.

| Product Example | Toluene | Chloroform | Water | DMF | $H_2SO_4$ | Acetone | m-Cresol |
|---|---|---|---|---|---|---|---|
| 1 | I | I | I | I | I (sw) | I | — |
| 3 | I | I | I | I (sw) | I (sw) | I | — |
| 4 | I | I | I | I | I (sw) | | — |
| 5 | I | I | I | I | I (p/d) | I | — |
| 7 | I | I | I | I | I | I | — |
| 8 | I | I | I | I | I (sw) | I | — |
| 9 | I | I (sw) | I (sw) | I (sw) | I (sw) | I (sw) | — |
| 10 | I | I (sw) | I (sw) | I (sw) | I | I | — |
| 11 | I | I | I | I | I (sw) | I | — |
| 12 | I (sw) | I (sw) | I | I (sw) | I (sw) | I | — |
| 13 | I | I | I | I | I (sw) | I | I |
| 14 | I | I | I | I | I (sw) | I | I |
| 15 | I (sw) | I (sw) | I | I | S (d) | I | — |
| 16 | I | I (sw) | I | I (sw) | I (sw) | I | — |
| A | S | — | — | — | — | — | — |
| B | S | — | — | — | — | — | — |
| C | S | S | — | — | — | S | — |
| D | — | S | — | — | — | — | — |
| E | — | — | S | — | — | — | — |
| F | — | S | — | S | — | — | — |
| G | S | — | — | S | — | — | — |
| H | — | — | — | — | S | — | S |
| I | — | — | — | — | S | — | S |
| J | — | — | — | — | S | — | S |

I: Insoluble
S: Soluble
sw: swollen
p: partially soluble
d: chemically degraded

As can be seen from the results tabulated above all of the products embodying the present invention are insoluble in a range of solvents. The very aggressive solvent concentrated sulphuric acid caused in a number of instances chemical degradation of the materials. By contrast the range of non-cross-linked samples were readily soluble.

We claim:

1. A process for preparing a three-dimensional porous polymeric material having a void space consisting of a three-dimensional network of cells separated from each other by walls and interconnected by holes through said walls, the cells having diameters in the range 100 to 0.5 μm, and the void space being in the range 75 to 98% of the total volume of the polymeric material, wherein the polymeric material is a cross-linked polycondensation polymeric material, said process comprising preparing an emulsion having a continuous phase containing polymerizable precursor materials for said polymeric material and an internal phase comprising 75 to 98 volume % of the emulsion and consisting of globules having dimensions in the range 100 to 0.5 μm and forming, in said continuous phase, by condensation polymerisation and condensation cross-linking, said cross-linked polycondensation polymeric material.

2. A process according to claim 1 including removing the internal phase.

3. A process according to claim 1 wherein the formation of the cross-linked polycondensation polymer is initiated by the addition of an acid or base to the emulsion or heating the emulsion or both.

4. A process according to claim 1 wherein the reactant materials to form the cross-linked polycondensation polymer are present in the emulsion being either both in the continuous phase or split between the phases.

5. A process according to claim 1 wherein the emulsion is prepared containing an acid or a base to initiate a polycondensation reaction.

6. A process according to claim 5 wherein the emulsion contains one reactant material in the continuous phase and is contacted with the second reactant material.

7. A process according to claim 1 wherein a polycondensation reaction is completed within 60 minutes.

* * * * *